US007510543B2

(12) United States Patent
Michels et al.

(10) Patent No.: US 7,510,543 B2
(45) Date of Patent: Mar. 31, 2009

(54) REMOVABLE SHARPS DEVICE FOR ACCESSING A PORTAL RESERVOIR

(75) Inventors: Lester D. Michels, Eden Prairie, MN (US); William L. Beling, Newbrighton, MN (US); Ronald G. Travis, Spring Lake Park, MN (US)

(73) Assignee: Smiths Medical MD, Inc., St. Paul, MN (US)

( * ) Notice: Subject to any disclaimer, the term of this patent is extended or adjusted under 35 U.S.C. 154(b) by 342 days.

(21) Appl. No.: 11/318,485

(22) Filed: Dec. 28, 2005

(65) Prior Publication Data

US 2007/0149921 A1 Jun. 28, 2007

(51) Int. Cl.
*A61M 5/00* (2006.01)
*A61M 31/00* (2006.01)
(52) U.S. Cl. .................................. 604/110; 604/93.01
(58) Field of Classification Search .............. 604/93.01, 604/110, 233, 239, 117, 131, 181
See application file for complete search history.

(56) References Cited

U.S. PATENT DOCUMENTS 4,813,939 A 3/1989 Marcus (Continued)

FOREIGN PATENT DOCUMENTS

| WO | 98/57683 | 12/1998 |
| WO | 99/62576 | 12/1999 |

*Primary Examiner*—Nicholas D Lucchesi
*Assistant Examiner*—Aarti Bhatia
(74) *Attorney, Agent, or Firm*—Louis Woo

(57) ABSTRACT

A portal access device that is adapted to provide long term access to a port implanted in a patient has two major components, an infuser assembly and a safety needle insertion device. The infuser assembly has an infuser housing that can be configured into a specific shape, for example a dome. A blunt cannula is attached to and extends downwardly from the underside of the infuser housing. Also connected to the infuser housing, preferably at a side thereof, is a tubing or catheter. The safety needle inserter assembly has a base having a proximal portion that is configured to form fit over the infuser housing. At the distal portion of the base uprights are provided so that a second end of an arm, to which first end a needle or a sharp cannula is connected, may be movably and hingedly connected to the base. The sharp cannula extends from the underside of the proximal end of the arm and passes through the base by way of a bore formed at the proximal portion of the base. The bore is defined between an opening at the underside of the base and an opening at the upper surface of the base. Locking mechanisms are provided at the base uprights and the distal end of the arm so that when the arm is moved away from the base, and as the distal end of the arm pivots about the uprights, the respective locking mechanisms provided at the arm and the base would coact to lock the arm in place, to thereby maintain the tip of the needle within the bore formed in the base. To use, the safety needle inserter is placed over the infuser assembly, with the sharp cannula extending through the infuser housing and axially mating with the blunt cannula of the infuser assembly, but with the tip of the sharp cannula protruding beyond the tip of the blunt cannula. The combined needle inserter/infuser assembly is pressed down onto the skin surface of the patient so that the combination sharp/blunt cannulas penetrate the patient and puncture the self-sealing septum of a portal reservoir implanted in the patient. Once the safety needle inserter is removed from the infuser assembly, with the infuser housing septum being self-sealing, a closed fluid communication path is established between the portal reservoir and a fluid store that may be connected to the catheter of the infuser assembly. Long term access of the implanted portal reservoir is thereby achieved.

24 Claims, 12 Drawing Sheets

U.S. PATENT DOCUMENTS

| | | | |
|---|---|---|---|
| 5,135,502 A | 8/1992 | Koenig, Jr. et al. | |
| 5,242,415 A | 9/1993 | Kantrowitz et al. | |
| 5,403,283 A | 4/1995 | Luther | |
| 5,562,617 A | 10/1996 | Finch, Jr. et al. | |
| 5,569,217 A | 10/1996 | Luther | |
| 5,607,407 A | 3/1997 | Tolkoff et al. | |
| 5,738,660 A | 4/1998 | Luther | |
| 5,743,891 A | 4/1998 | Tolkoff et al. | |
| 5,853,394 A | 12/1998 | Tolkoff et al. | |
| 5,858,001 A | 1/1999 | Tsals et al. | |
| 5,989,239 A | 11/1999 | Finch et al. | |
| 5,997,524 A | 12/1999 | Burbank et al. | |
| 6,039,712 A | 3/2000 | Fogarty et al. | |
| 6,053,901 A | 4/2000 | Finch, Jr. et al. | |
| 6,120,492 A | 9/2000 | Finch et al. | |
| 6,186,982 B1 * | 2/2001 | Gross et al. | 604/132 |
| 6,500,150 B1 * | 12/2002 | Gross et al. | 604/131 |
| 6,607,511 B2 | 8/2003 | Halseth et al. | |
| 6,613,015 B2 | 9/2003 | Sandstrom | |
| 6,676,633 B2 | 1/2004 | Smith et al. | |
| 6,719,721 B1 | 4/2004 | Okazaki | |
| 6,736,797 B1 | 5/2004 | Larsen et al. | |
| 6,926,693 B2 * | 8/2005 | Enns | 604/165.03 |
| 2002/0095138 A1 * | 7/2002 | Lynch et al. | 604/890.1 |
| 2002/0123740 A1 * | 9/2002 | Flaherty et al. | 604/890.1 |
| 2003/0069546 A1 | 4/2003 | Sandstrom | |
| 2004/0049159 A1 | 3/2004 | Barrus et al. | |
| 2005/0049553 A1 | 3/2005 | Triplett et al. | |
| 2006/0200073 A1 * | 9/2006 | Radmer et al. | 604/93.01 |
| 2006/0253076 A1 | 11/2006 | Butts et al. | |
| 2006/0264898 A1 | 11/2006 | Beasley et al. | |
| 2007/0149920 A1 * | 6/2007 | Michels et al. | 604/93.01 |

* cited by examiner

REMOVABLE SHARPS DEVICE FOR ACCESSING A PORTAL RESERVOIR

FIELD OF THE INVENTION

The present invention relates to a device for accessing a portal reservoir, and more particularly a portal access device that combines long term accessing of a portal reservoir with sharps protection.

BACKGROUND OF THE INVENTION

Long term intravenous therapy to a patient oftentimes requires that a portal reservoir (also may be referred herein as port or portal) be implanted to the patient. The medicament stored in the port is fed slowly to the patient via a catheter connected to the portal. To refill the portal, conventionally a needle is inserted through the skin of the patient into a septum of the portal so that the portal may be refilled with the desired medicament. As with the use of any needle or sharps instruments, there is always a chance that the user, or a bystander, may be accidentally pricked by the contaminated needle when it is removed from the patient. Such accidental injury may well be serious as the tip of the needle is contaminated with the fluid from the patient.

A prior device used for shielding the contaminated tip of the needle is disclosed in U.S. Pat. No. 6,613,015, assigned to the assignee of the instant application and marketed under the trade name GRIPPER PLUS. The disclosure of the '015 patent is incorporated by reference herein. In the '015 patent, a right angle needle for accessing the portal is disclosed. The '015 device has the horizontal portion of its right angle needle embedded in an arm that has a distal portion hingedly connected to uprights of a base. The vertical portion of the needle extends through an opening at the proximal portion of the base. Medicament or fluid is fed to the right angle needle via a catheter connected to the distal end of the horizontal portion of the needle. A well or catch is formed above the main body of the base adjacent the opening so that when the arm is pivotally raised relative to the base and when the needle is fully pulled out of the base, the tip of the needle would flex forward so as to be entrapped in the catch adjacent to the opening. Even though surrounded by a dam, the tip of the needle nonetheless is exposed to the environment and viewable by the patient, and there is a remote chance that contaminated fluid at the tip of the needle may adhere to the well, or may be splattered unnecessarily around the area of the well or beyond. A similar right angle device is disclosed in U.S. Pat. No. 6,719,721.

After accessing the portal and refilling it, the device of the '015 patent is removed from the skin of the patient. Any subsequent refilling of the portal requires that a new right angle needle device be used to gain access to the portal. This repeated insertion of a needle to the patient tends to cause discomfort, at the very least, to the patient.

There is therefore a need for a portal access device that may be secured to the patient on a long term basis so as not to subject the patient to repeated inserts by needle sharps.

There is also a need for a sharps protection device having the tip of its needle that, once removed from the patient, will not be exposed to the environment or seen by the patient.

SUMMARY OF THE PRESENT INVENTION

The portal access device of the instant invention comprises two main components that may or may not be preassembled prior to shipping. The first of these components incorporates a safety needle insertion device similar to the device disclosed in the above incorporated by referenced '015 patent, but with modifications. The second component is a low profile portal access assembly that includes an infuser or a cap, a blunt cannula extending downwardly from the infuser, and a flexible delivery tubing or catheter connected to the infuser for establishing a fluid path between the conduit and the blunt cannula. The blunt cannula, or at least a tip portion thereof, is to be piercingly coupled to the portal reservoir so that fluids, or medicaments, may be delivered to or removed from the portal reservoir by way of the infuser.

The main body of the infuser, or its cap or housing, is the portion of the component external to the patient and is meant to be positioned on or above the patient's skin surface, along with its attached tubing. The blunt cannula is attached to and extends downwardly from the infuser housing through the skin of the patient and the portal septum after placement, and establishes the fluid communication path between the external tubing of the infuser assembly and the portal reservoir implanted in the patient.

To be properly inserted to the patient, the needle sharps device is superposed, or fits, over the infuser in such a way that its needle or sharp cannula extends past the self sealing septum of the infuser, through the infuser, and axially into the blunt cannula, with the tip of the sharp cannula protruding or exposed from the end of the blunt cannula. The sharp cannula thereby serves as the means to puncture and penetrate first the patient and then the self sealing septum at the portal reservoir to provide a track for the coaxial blunt cannula. Once the sharp cannula and the blunt cannula, or at least corresponding portions of the respective tips thereof, are coaxially positioned correctly within the portal reservoir, the sharp cannula is removed from the blunt cannula. Once the sharp cannula is removed from the infuser assembly, the safety needle protection device may be removed from the infuser assembly. The tip of the needle or sharp cannula is fixedly maintained within a bore of the base of the needle insertion device that extends between the opening at the top surface and the opening at the lower surface of the base wherethrough the sharp cannula extends into the blunt cannula.

Respective locking mechanisms are provided at the end of the arm of the needle insertion device that connects to the base and the uprights at the base to which the arm is hingedly or pivotally connected to prevent the arm from further movement, be it upwards or downwards, relative to the base once the tip of the needle is positioned within the bore of the base. The sharps protection device may then be safely and properly discarded.

The infuser assembly remains on the patient, with the septum of the infuser where the sharp cannula entered and exited self-sealed. With proper attachment to the patient, either adhesively or by tape, the low profile infuser assembly provides long term access to the portal reservoir without further risks of sharps injury, or further unnecessary pain and discomfort, to the patient due to the need for reinsertions of sharp needles to the patient.

To hide the contaminated tip of the needle or the sharp cannula from the user and also the patient, the needle insertion device of the instant invention is configured such that when the tip of the contaminated needle is withdrawn first from the portal reservoir and then the patient, as soon as it is positioned appropriately in the bore formed in the base through which the sharp needle or cannula extends, the movement of the arm that bears the sharp cannula is stopped and locked into place, so that the tip of the needle would not come into contact with any part of the base, and is not withdrawn above the top surface, or the opening at the top surface, of the base. Locking mechanisms at the end of the arm that hingedly connects to the base and at the uprights to which the arm is hingedly attached cooperatively coact to prevent any further upward and downward movements of the arm, once the tip of the needle is appropriately positioned within the bore.

The lower surface of the base of the needle insertion device is configured to form fittingly mount over the infuser, both the infuser or cap portion and the tube connecting thereto that lie over the patient's skin surface, so that the needle injection device and the infuser may be pre-assembled as a unit.

A first aspect of the instant invention is a combination of an infuser, or a fluid storage housing or body, to which a blunt cannula is connected and to which a tube extends, so that the infuser establishes a fluid communication path between the blunt cannula and the tube. The combination further includes a sharp cannula that is removably mated to the blunt cannula through the infuser with the tip of the sharp cannula protruding or extruding beyond the tip of the blunt cannula. The sharp cannula is attached to a first end of a arm, a second end of which being movably connected to a distal portion of a base. The sharp cannula extends through an opening at a proximal portion of a base which is configured to fit over the infuser when the sharp cannula is mated to the blunt cannula. The sharp cannula is removable from the blunt cannula when the first end of the arm is moved in a direction away from the proximal portion of the base.

The invention also relates to an apparatus that comprises an infuser having a blunt cannula extending downwardly therefrom and a tube connected thereto for establishing a fluid communication path between the tube and the blunt cannula; and an insertion device that includes a base having a distal portion and a proximal portion, an arm having a second end hingedly and movably connected to the distal portion of the base, a sharp cannula attached to a first end of the arm, an opening provided at the proximal portion of the base, with the base covering the infuser and the sharp cannula removably mated to the blunt cannula through the opening at the proximal portion of the base, and the tip of the sharp cannula protruding or exposed beyond the tip of the blunt cannula when the arm lies substantially longitudinally along the base. The sharp cannula is removable from the blunt cannula when the first end of the arm is moved pivotally in a direction away from the base.

The invention further relates to a method of establishing a fluid path between a fluid store and a port or portal reservoir implanted in a patient. The method comprises the steps of: (a) providing a blunt cannula extending downwardly from an infuser and a tube having one end connected to the infuser and another end connected to a fluid store so that the tube is in fluid communication with the blunt cannula, (b) providing a base having a sharp cannula, (c) superposing the base over the infuser and removably mating the sharp cannula to the blunt cannula until the tip of the sharp cannula is exposed beyond the tip of the blunt cannula, (d) inserting the combined sharp and blunt cannulas to a patient to position the respective tips of the cannula into the port, and (e) removing the sharp cannula from the blunt cannula while leaving at least the tip of the blunt cannula in the port, so as to establish a fluid communication path between the port and the fluid store through the blunt cannula and the infuser.

The invention furthermore relates to an apparatus comprising an infuser housing adaptable for storing fluids, a blunt cannula extending downwardly from the housing, and a tube connected to a side of the housing for establishing a fluid path between the tube and the blunt cannula through the housing.

The needle insertion device of the instant invention relates to an apparatus that comprises a base having a distal portion and a proximal portion, a cannula attached to a first end of an arm, a second end of the arm hingedly connected to the distal portion of the base so that the arm is pivotable relative to the base at its second end, an opening provided at the proximal portion of the base wherethrough the cannula passes, a bore extending from the opening at the proximal portion of the base, a first lock mechanism or a first portion of a lock mechanism(s) provided at the distal portion of the base and a second lock mechanism or a second portion of a lock mechanism(s) provided at the second end of the arm, the first and second lock mechanisms coacting to prevent movement of the arm relative to the base after the tip of the cannula moves past the opening and is within the bore.

The needle insertion device of the instant invention is further a safety needle device that comprises a base having a distal portion and a proximal portion, an opening provided at the proximal portion of the base, a bore extending from the opening at the proximal portion of the base, an arm having a first end and a second end, the second end of the arm being hingedly connected to the distal portion of the base so that the arm is pivotally moveable relative to the base at its second end; and a right angle cannula mounted to the arm, a vertical portion of the cannula including the tip of the cannula extending downwardly from the first end of the arm and passes through the opening of the base before use, a horizontal portion of the cannula mounted along the length of the arm, so that when the first end of the arm is moved to its upmost position, the vertical portion of the cannula is withdrawn from the opening and the tip of the cannula is positioned within the bore.

The safety needle device of the instant invention may further include a first lock mechanism having a first and second part provided at the distal portion of the base, and a second lock mechanism having a first and second part provided at the second end of the arm with the respective first parts of the first and second lock mechanisms coacting to prevent further movement of the arm relative to the base along one direction after the tip of the cannula is positioned within the bore, and the respective second parts of the first and second lock mechanisms coacting to prevent further movement of the arm relative to the base along another direction once the tip of the cannula is positioned within the bore.

It is therefore an objective of the present invention to provide a portal access device that alleviates the need to reinsert a sharp cannula in the patient every time there is a need to either remove fluid from, or infuse fluid into, the portal reservoir implanted in the patient.

It is another objective of the present invention to provide a portal access device which needle insertion portion may be safely removed after the port has been accessed.

It is yet another objective of the present invention to provide a portal access device that allows a medical personnel to readily gain access to a portal reservoir implanted in a patient to clean out any obstruction that might occlude the flow of fluid into or out of the portal reservoir.

It is a further objective of the instant invention to provide a needle insertion device configured to prevent the tip of the contaminated needle or cannula from touching any part of the base of the device, and from being exposed to the environment or viewed by the patient or the user once the sharp cannula is withdrawn from the infuser portion of the portal access device.

BRIEF DESCRIPTION OF THE FIGURES

The present invention will become apparent and the invention itself will be best understood by reference to the following description of the present invention taken in conjunction with the accompanying drawings, wherein.

DETAILED DESCRIPTION OF THE INVENTION

Figure 1:
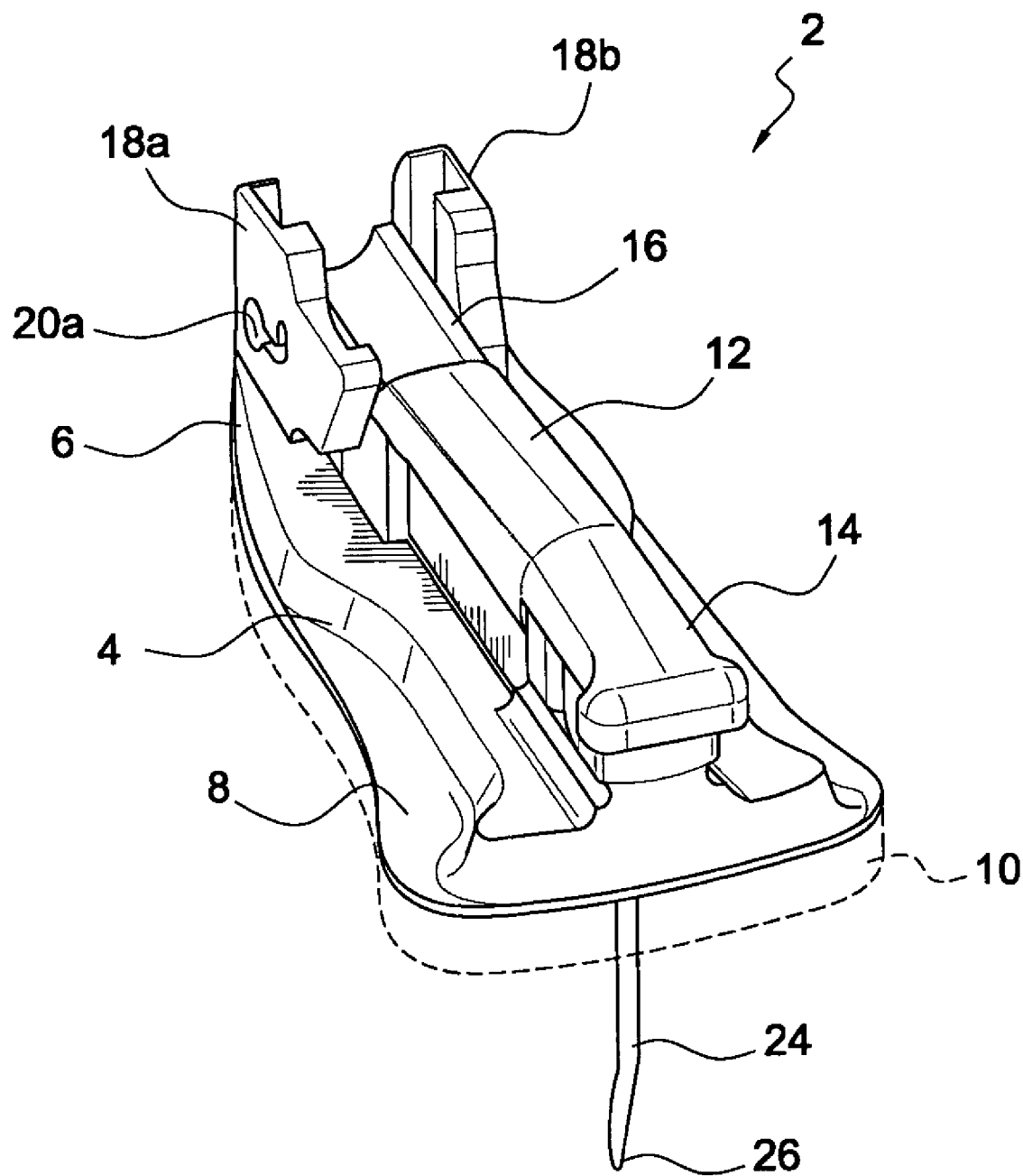
FIG. 1 is a perspective view of the safety needle inserter device of the instant invention.
Figure 2:
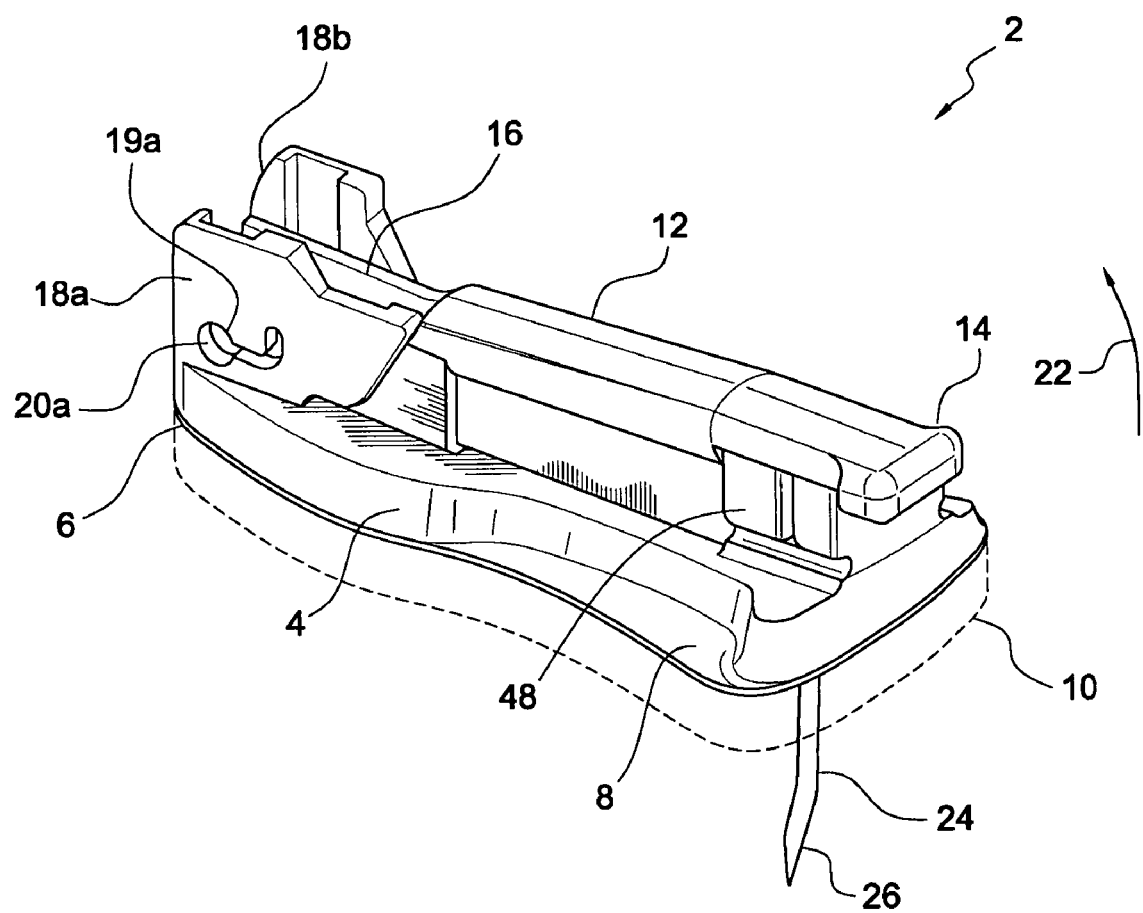
FIG. 2 is a perspective view of a first embodiment of the safety needle inserter of the instant invention.

The first embodiment of the safety needle inserter device component of the instant invention is shown in FIGS. 1-4. As shown, the safety needle inserter 2 has a base 4 that has a distal portion 6 and a proximal portion 8. A foam pad or layer 10 coated with an adhesive for adhering base 4 to the patient may be mounted to the underside, or the lower surface, of base 4. An arm having a first end 14 and a second end 16 is hingedly connected to two uprights 18a and 18b, respectively, at distal portion 6 of base 4. Two lugs 19, one at each side of second end 16 of arm 12, are movably journaled to the respective guide holes 20a and 20b of the respective uprights 18a and 18b, to thereby hingedly and movably connect arm 12 to base 4. Only lug 19a is shown in FIG. 2. When uplifted in the direction as indicated by directional arrow 22, arm 12 is pivotally moved, via its second end 16, in an upward direction relative to base 4.

A needle, or sharp cannula, 24, is mounted to the underside of arm 12, at its first end 14. As shown in FIGS. 1 and 2, when arm 12 lies substantially longitudinally along the length of base 4, needle 24 extends downwardly from base 4 through an opening 44, best shown in the embodiment of FIG. 5. As shown, sharp cannula 24 has a tip 26 that is adapted to insert into the patient and penetrate the septum of a portal reservoir, or port, implanted to a patient. Note that even though the sharp cannula 24 of the safety needle inserter of the FIGS. 1-4 embodiment is a unitary needle mounted vertically from arm 12, a right angle needle that has a vertical portion and a horizontal portion embedded in arm 12 may also be used as the safety needle inserter of the instant invention. In the case where a right angle needle is used, the distal end of the horizontal portion of the right angle needle may be connected to a catheter, tube or tubing so that fluid may be conveyed to, or removed from, the sharp cannula 24. The sharp cannula may be usable singly, or coaxially with a blunt cannula of the to be discussed infuser component of the instant invention.

Figure 3:
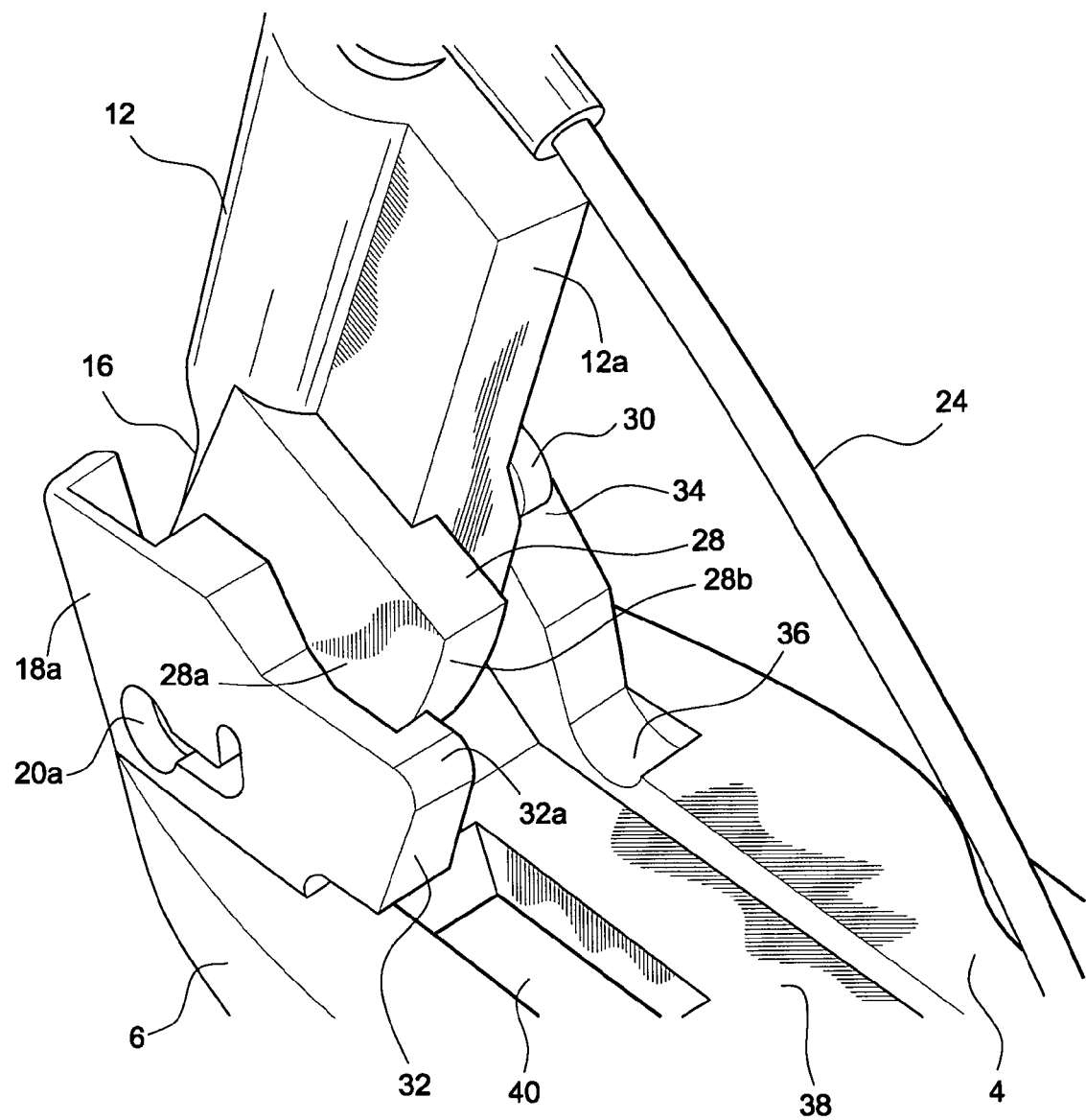
FIG. 3 is an enlarged view of the interconnection between the base and the arm of the safety needle inserter of the instant invention.
Figure 4:
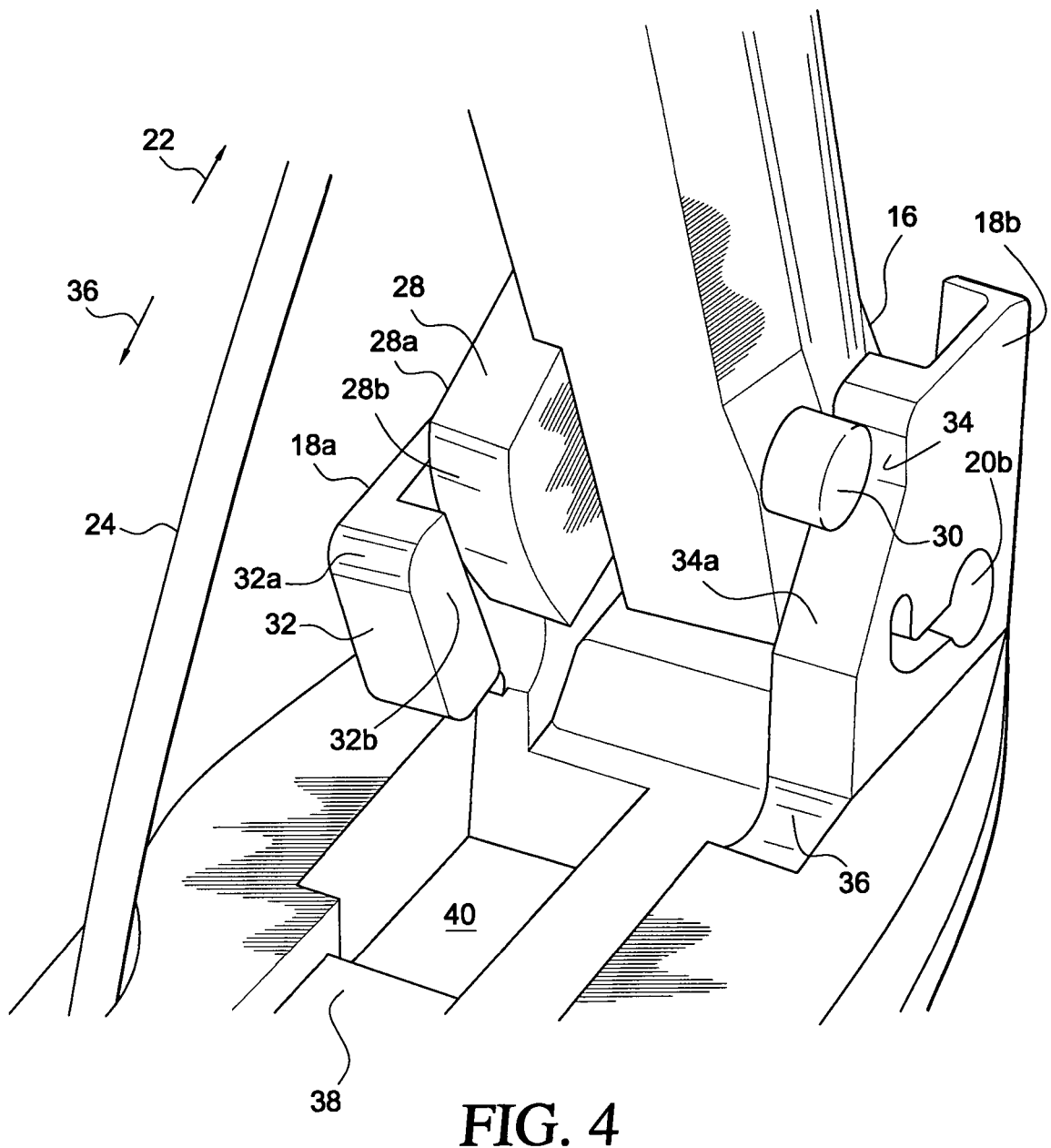
FIG. 4 is another view of the interconnection between the arm and the base of the safety needle inserter of the instant invention.
Figure 5:
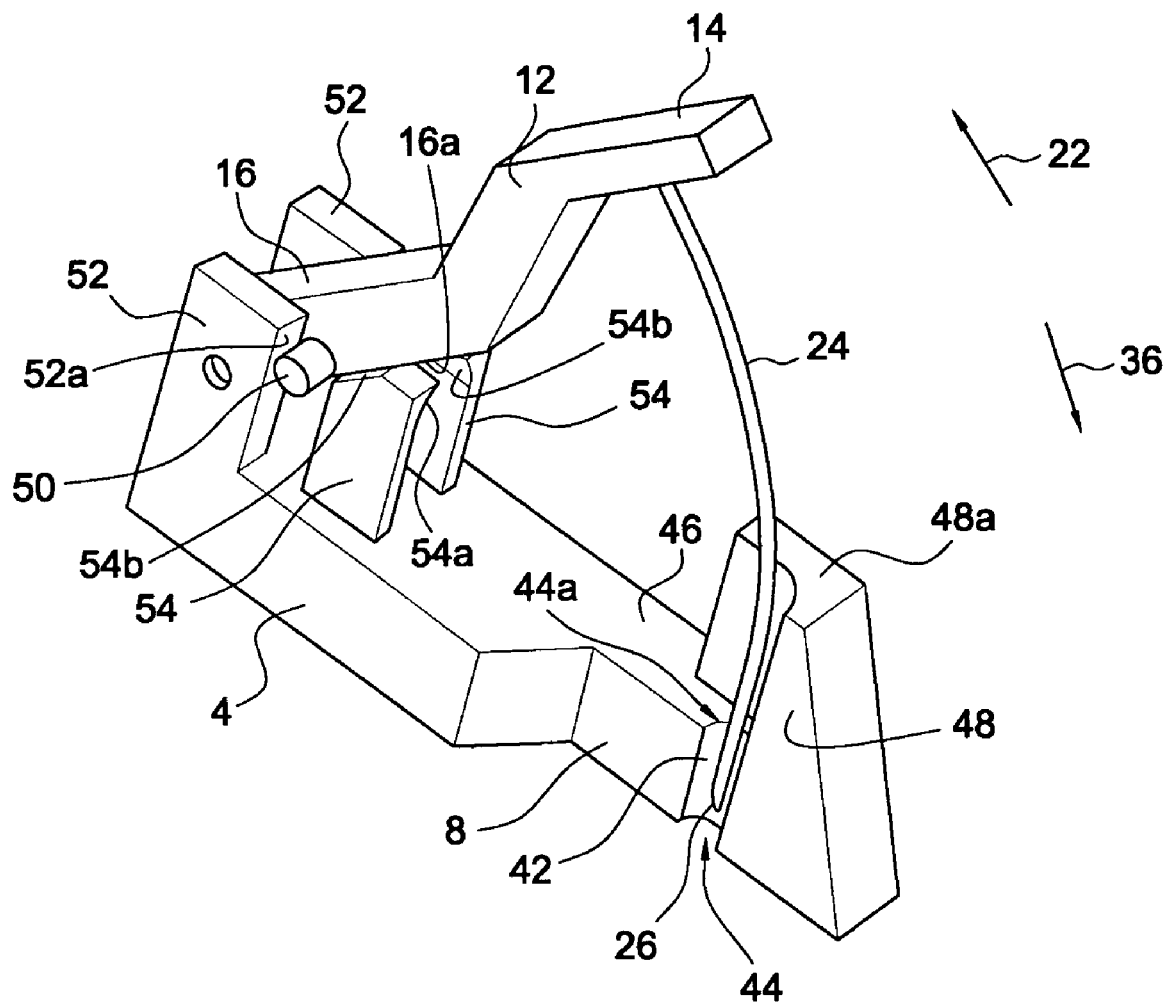
FIG. 5 is another embodiment of the safety needle inserter of the instant invention showing in particular the location of the tip of the needle, or sharp cannula, positioned within the bore of the base.

FIGS. 3 and 4 illustrate the locking mechanisms at the respective uprights 18a and 18b at distal portion 6 of base 4 and the corresponding coacting locking mechanisms formed at end 16 of arm 12 for preventing further movement of arm 12, once it has been pivotally moved relative to base 4 when tip 26 of sharp cannula 24 is positioned within a bore 42 formed in base 4, best illustrated in the embodiment of the safety needle inserter shown in FIG. 5. Although disclosed as different lock mechanisms, the different portions at both arm 12 and uprights 18 of base 4 may be considered as different parts of a single locking mechanism that cooperatively work together to lock arm 12 in place relative to base 4, and more importantly to fixedly maintain tip 26 of sharp cannula 24 within bore 42 formed at proximal portion 8 of base 4, so as to prevent tip 26 from being exposed or fluid thereon from being splattered, when sharp cannula 24 is withdrawn from the patient.

In particular, the lock mechanisms, or the portions of the lock mechanism, as shown in the FIGS. 3 and 4 embodiment, comprise a leg 28 and a boss 30 at the respective sides of end 16 of arm 12. The lock mechanisms, or the parts of the lock mechanism, at distal portion 6 of base 4 are configured as a shoulder 32 at upright 18a and a groove or recess 34 at upright 18b.

Due to the inherent elasticity in the medical plastics that are used for form molding the base and the arm of the safety needle insertion device, when arm 12 is moved along the direction indicated by directional arrow 22, the side surface 28a of leg 28 would bias against the surface 32a of leg 32, as boss 30 may or may not be sliding along surface 34a of groove 34, so that once the foot 28b of leg 28 passes ledge 32b of shoulder 32, shoulder 32 will return to its original position so that latch 32b and foot 28b would bias or coact against each other to prevent any downward movement, as indicated by directional arrow 36, of arm 12. At substantially the same time, once boss 30 reaches groove 34 and biases thereagainst, further upward movement of arm 12 relative to base 4 is prevented.

To enable arm 12 to lie co-planarly on base 4, a notch 36 is provided on base 4 as a rest for boss 32. Further, a channel 38 is molded into base 4 to allow the downward extending portion 12a of arm 12 to fit in alignment to base 4, when arm 12 is in the position vis-a-vis base 4 as shown in FIGS. 1 and 2. A void 40 is provided on base 4 to receive leg 28 of arm 12 so that arm 12 could lie substantially along base 4 as shown in FIGS. 1 and 2.

FIG. 5 is an illustration of a second embodiment of the safety needle inserter of the instant invention. Other than the overall look of the safety needle inserter and the various parts of the locking mechanisms which coact to lock arm 12 in place relative to base 4, the safety needle inserter of the FIG. 5 embodiment functions in the same way as the embodiment shown in FIGS. 1-4. The components that are the same as those of the earlier disclosed embodiment are labeled the same.

As shown more clearly by the partial cut-away view, the tip 26 of sharp cannula 24, when withdrawn from the portal reservoir and the patient, is maintained within a bore 42 that is formed at the proximal portion 8 of base 4. As shown, bore 42 is defined between opening 44 at the underside or lower surface of base 4 and an opening 44a at the upper side or upper surface 46 of base 4. A dam 48 extends from proximal portion 8 of base 4 and serves as an additional safety feature to ensure that the tip 26 of cannula 24 could not be forcibly removed from bore 42. In addition, the top 48a of dam 48 provides a rest stop for arm 12, with end 14 thereof resting against top surface 48a, when needle 26 is axially fitted to the blunt cannula of the infuser. Dam 48 also provides a point for the needle inserter where a user can apply the force needed to insert the sharp cannula into the patient and, as will be described infra, penetrate the septum of the portal reservoir implanted to the patient. The same dam structure is provided in the earlier embodiment of the safety needle inserter.

The FIG. 5 embodiment of the safety needle inserter is different from the embodiment shown in FIGS. 1-4 in that instead of using separate components for preventing upward and downward movements of arm 12, a pair of bosses 50 provided at the end 16 of arm 12 would bias against the respective front faces 52a of a pair of uprights 52 that are formed at the distal portion of base 4, to prevent further upward movement of arm 12 relative to base 4. A second pair of uprights 54 also extend from base 4 to grasp arm 12, when arm 12 lies longitudinally along base 4 with cannula 24 extending though opening 44. The holding of arm 12 by uprights 54 is by way of corresponding fingers 54a and 54b at the uprights 54. Since uprights 54, along with base 4 and arm 12, are all molded from medical plastics material, when arm 12 is moved upwardly per directional arrow 22, fingers 54b of the uprights 54 would give away until end portion 16 of arm 12 passes both fingers 54a and 54b. At which time uprights 54 would return to their respective original positions so that the lower surface 16a of end portion 16 of arm 12 would rest against the respective inclines 54b of uprights 54, thereby preventing arm 12 from any downward movement as indicated per directional arrow 36.

Figure 6:
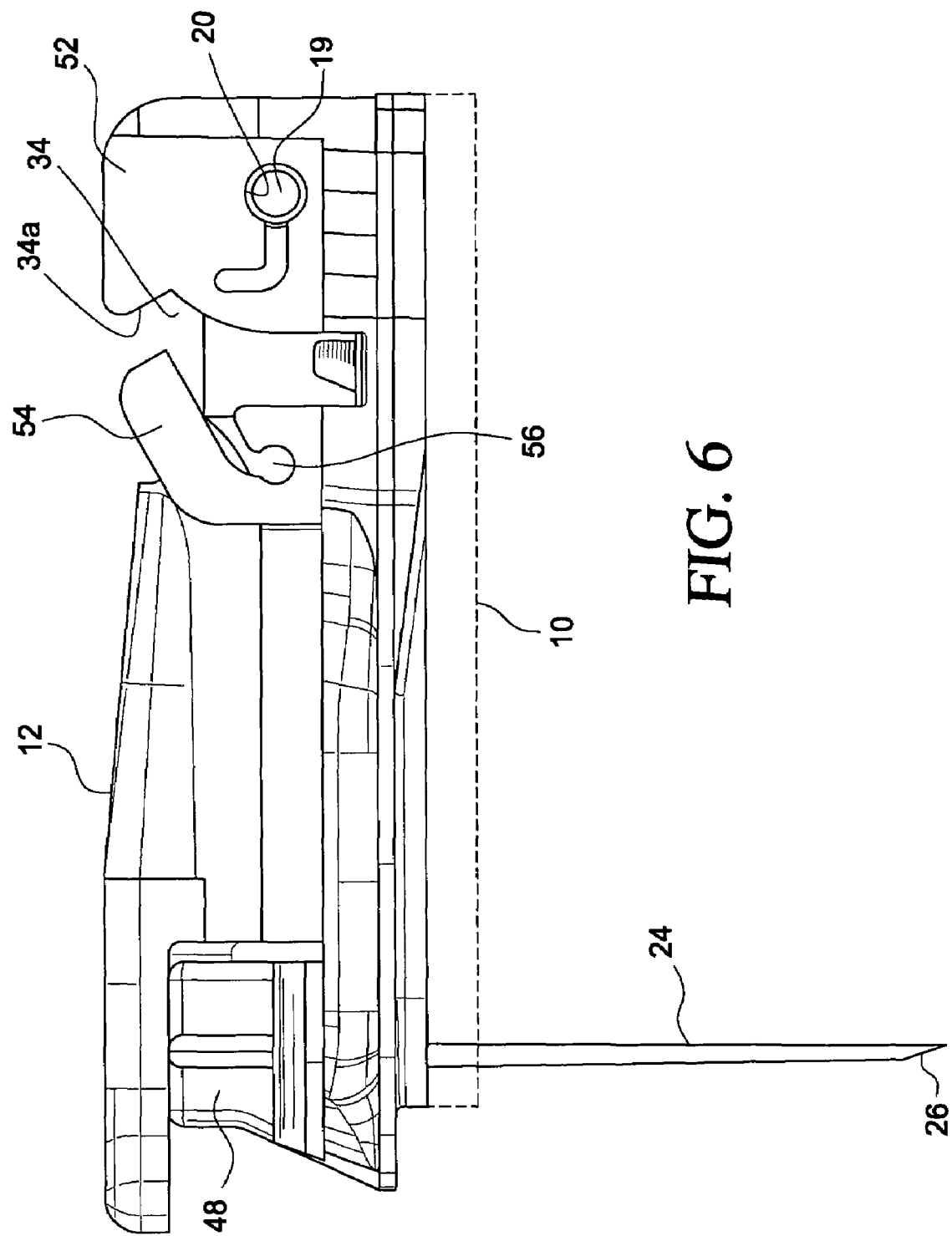
FIG. 6 is a side view of another embodiment of the safety needle inserter of the instant invention, with the arm of the inserter shown lying longitudinally along the base and the sharp cannula extending downwardly from the base.
Figure 7:
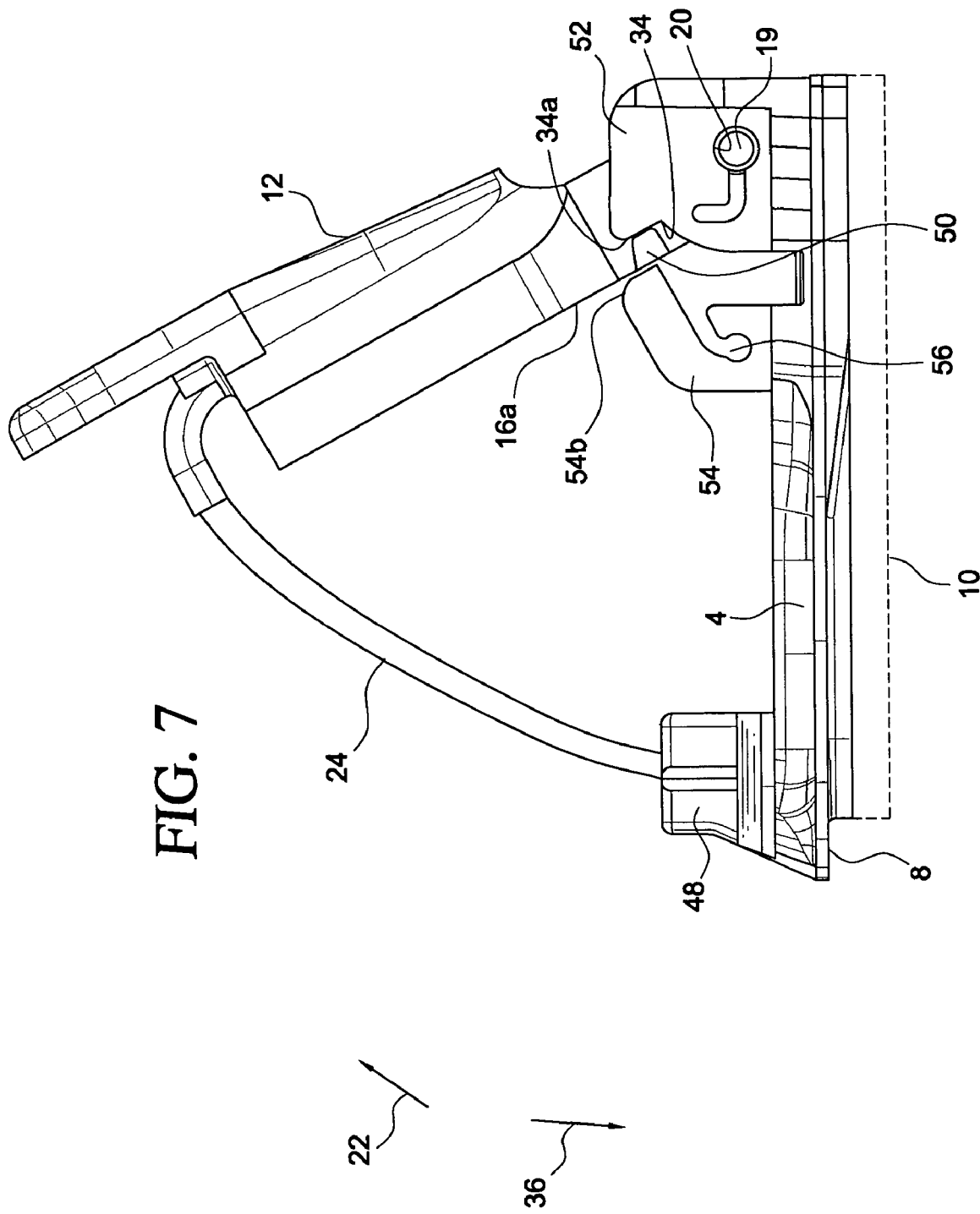
FIG. 7 is another view of the safety needle inserter of the FIG. 6 embodiment showing the sharp cannula having been withdrawn from the opening of the base with the tip residing within the bore of the base and the arm having been pivoted upwardly relative to the base.
Figure 8:
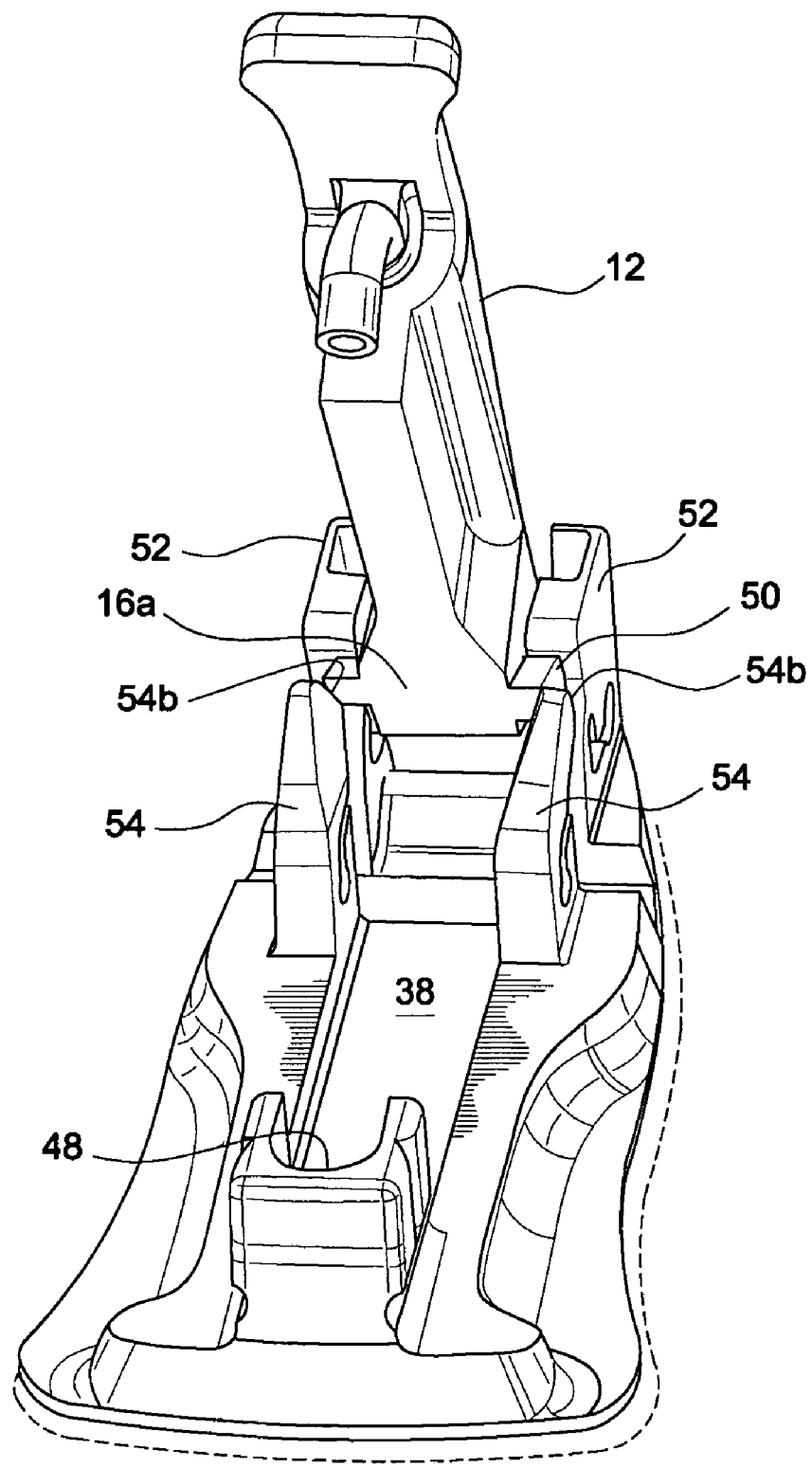
FIG. 8 is a front perspective view of the safety needle inserter of FIGS. 6 and 7, sans the sharp cannula, for showing the interrelationship between the locking mechanisms at the uprights of the base and the end of the arm hingedly connected to the uprights of the base.

A third embodiment of the safety needle inserter of the instant invention is shown in FIGS. 6-8. This embodiment is a modification of the simplified embodiment shown in FIG. 5 in that uprights 54 have been reconfigured to allow additional flexibility by the adding of a notch 56 thereto. As a consequence, when arm 12 is pulled upwards along the direction as indicated by directional arrow 22, each of uprights 54 would tend to flex away, until the underside 16a of arm 12 clears the top edge 54b of the respective uprights 54. At which time, uprights 54 will return to their respective memorized original positions so as to move upper surfaces 54b of uprights 54 under the bottom surface 16a of arm 12 and more specifically those surfaces of the bosses 52, or areas proximate thereto, to thereby prevent downward movement of arm 12 along the direction as indicated by directional arrow 36.

Further, similar to the embodiment shown in FIGS. 1-4, respective grooves or recesses 34 are provided at the uprights 52, so that bosses 52 are caught by the front surfaces of the respective recesses 34, designated by 34a, so as to prevent arm 12 from any further upward movement as indicated by directional arrow 22. As before, even though not shown for the sake of clarity, the tip of needle 24 is fixedly retained within a bore at proximal portion 8 of base 4. Note that FIGS. 6-8 clearly show that arm 12 is hingedly connected to base 4 by way of its lugs 19 movably journaled to apertures 20 of uprights 52.

As with the other embodiments, a foam layer or pad 10 with an adhesive underside may be provided to the safety needle inserter for enhancing the comfort to the patient, when the inserter is used individually. However, as will be discussed infra, the fact that the safety needle inserter is a component of the overall portal access device of the instant invention, and its lower surface does not come into contact with the patient when used with the infuser component, foam 10 is not needed when the safety needle inserter is to be used with the infuser.

Figure 9:
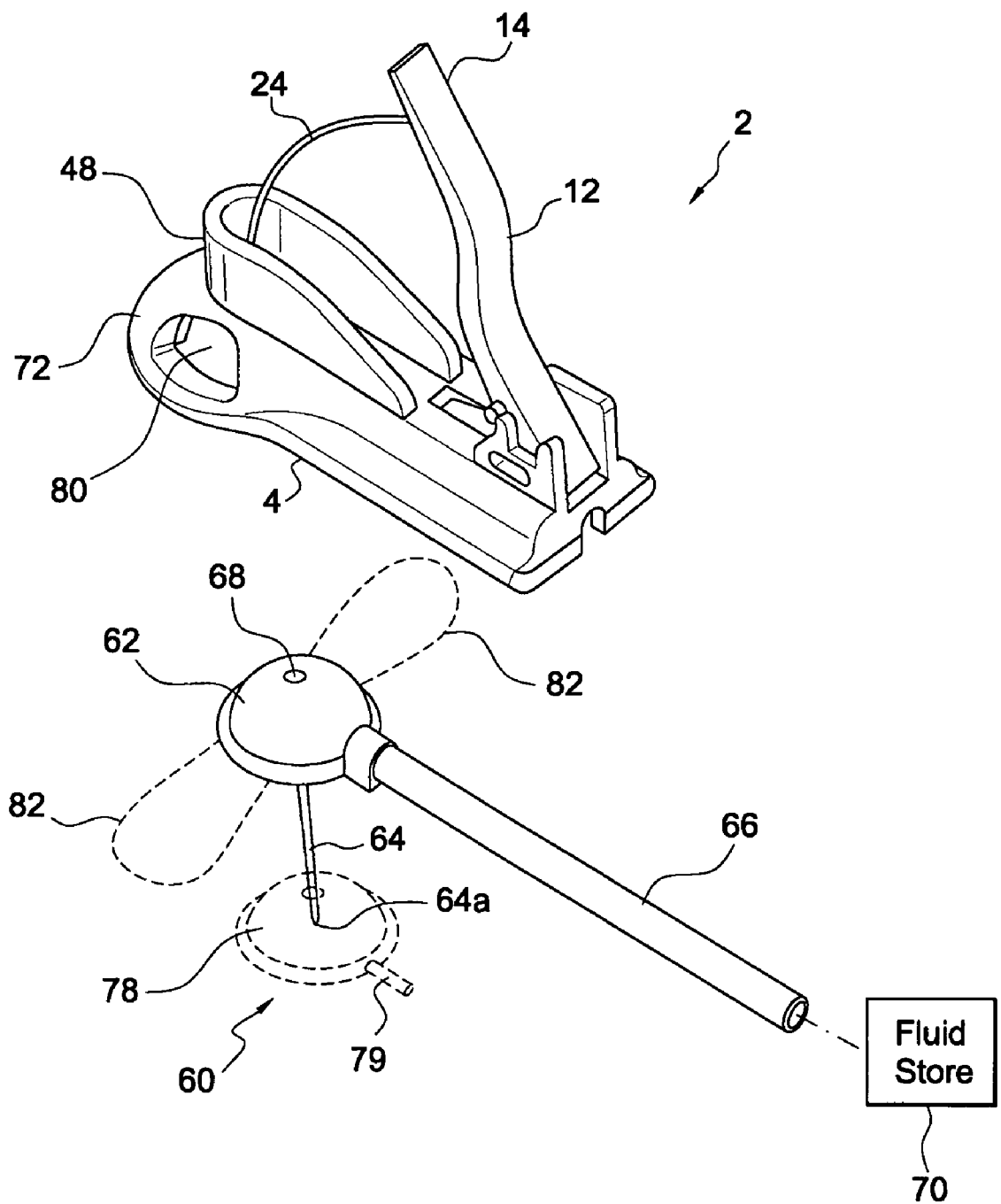
FIG. 9 shows the portal access device of the instant invention in which the safety needle inserter component of the instant invention is superposed over an infuser assembly component of the instant invention.

With reference to FIGS. 9-12, the portal access device of the instant invention is shown. In particular, a safety needle inserter 2 as described above is used in conjunction with an infuser or a low-profile portal access assembly 60 that includes an infuser body or housing 62, a blunt cannula 64 attached to the underside of body 62 and a catheter or tube 66 that is attached to a side of body 62. As shown in FIG. 9, infuser body 62 is formed as a domed shaped housing or a manifold that has a self-sealing septum 68 at its top in axial alignment with blunt cannula 64. Given that housing 68 is substantially hollow, infuser 60 in essence provides a fluid storage depot through which a communication path between tube 66 and blunt cannula 64 is established.

In operation, tube 66 is connected to a fluid store 70, which may be a syringe or a pump or some other storage device that is adapted for storing fluids or medicaments to be infused to the patient. Alternatively, instead of infusing fluid to the patient, or more particularly to the portal reservoir which is punctured by blunt cannula 64, fluid in the portal reservoir may be retrieved by means of the fluid communication path established between blunt cannula 64 and tube 66 via infuser body 62.

The safety needle inserter component of the portal access device of the instant invention, for the FIG. 9 embodiment, has its proximal portion configured as a dome 72 so that it may be form fitted over infuser body 62. Of course, infuser body 62 may have different dimensions and be configured as different shapes, for example a rectangular shaped housing. In which case, the proximal portion of base 4 of the safety needle inserter would also be rectangularly shaped so that it may form fit over the hypothetical rectangular shaped infuser body. Further, the remainder portion of base 4 may be configured to fit over tube 66, by having a channel 74 formed at its underside as shown by the bottom view of the safety needle inserter in FIG. 10.

Figure 10:
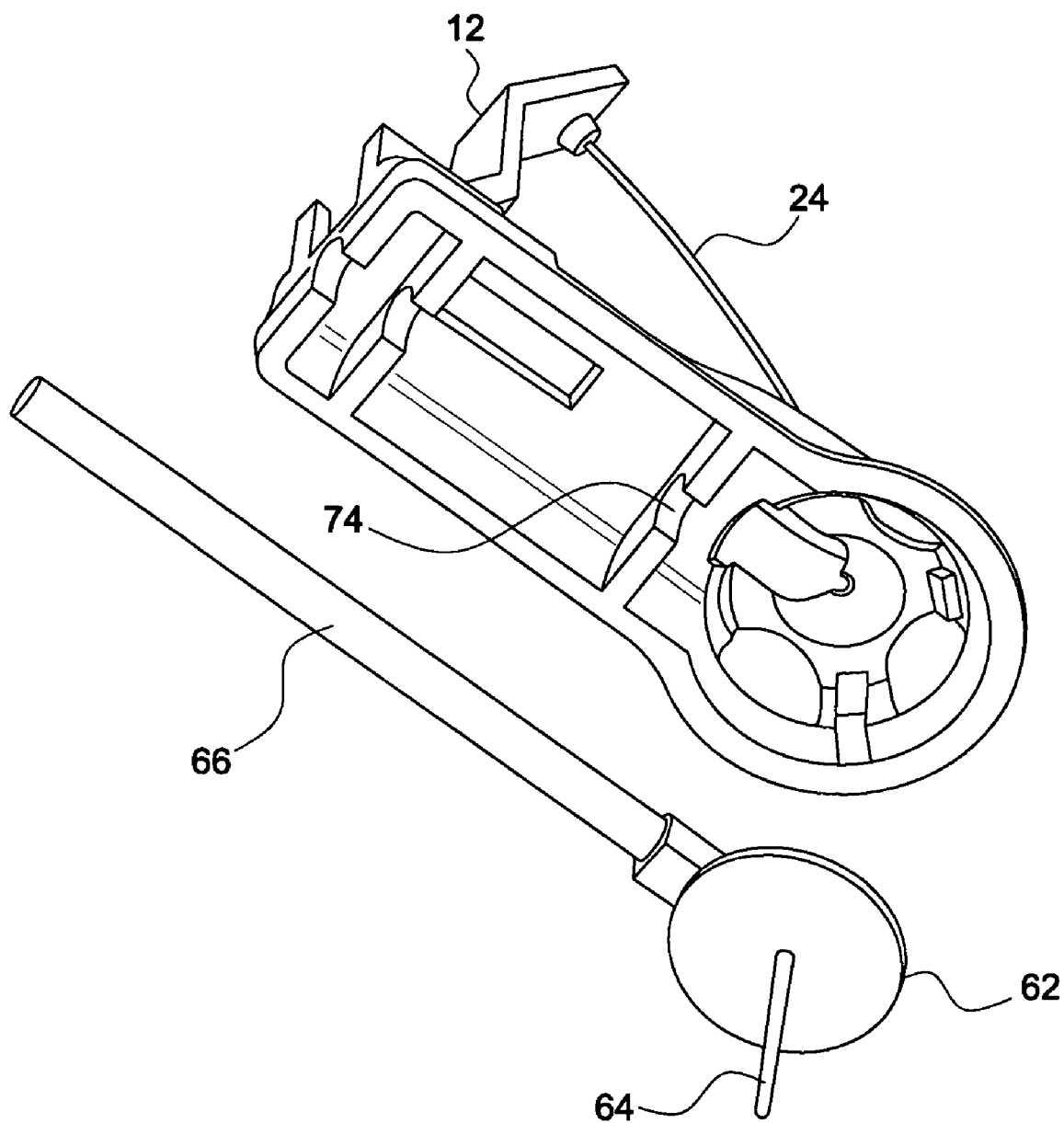
FIG. 10 is a bottom view of the portal access device of the instant invention showing in particular the underside of the infuser and the safety needle inserter.

The operation of the safety needle inserter component of the portal access device as shown in FIGS. 9 and 10 is the same as that discussed earlier with respect to the various embodiments of the safety needle inserter. When used with infuser assembly 60, safety needle inserter 2 is placed over infuser assembly 60 so that needle or sharp cannula 24 of the needle insertion device 2 is inserted through septum 68 into infuser body 62 and axially through blunt cannula 64 until the tip 26 of sharp cannula 24 protrudes or is exposed beyond the tip 64a of blunt cannula 64. By configuring the proximal portion of needle inserter 2 to form fit over the infuser housing 62, and with arm 12, in particular proximal portion 14 thereof, resting on dam 48 of base 4, a user can readily insert the combination blunt cannula 64/sharp cannula 24 into a patient, designated by 74 in FIGS. 11 and 12, so that the tip 26 of cannula 24 may be inserted through a septum opening 36 of a port or portal reservoir 78 implanted in patient 74, per shown in FIGS. 11a and 12a. A window 80 may be formed at the proximal portion 8 of base 4 to enable the user to confirm that the dome 72 of the safety needle inserter 2 is appropriately form fitted over infuser body 62, to thereby ensure that cannula 24 be inserted correctly into infuser body 62 and through blunt cannula 64.

Figures 11A, 11B:
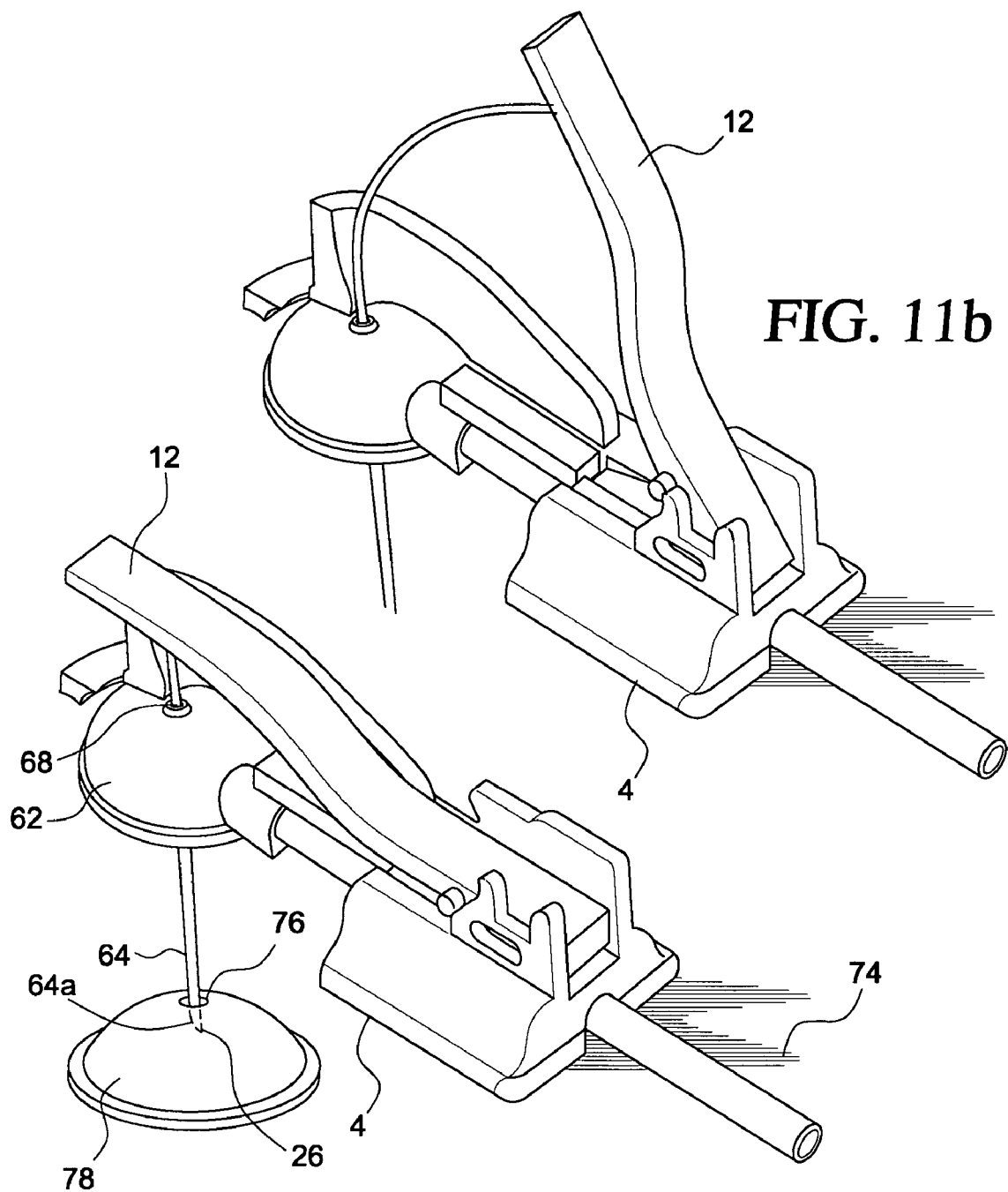
FIG. 11a and FIG. 11b show the sharp cannula of the safety needle inserter mated axially to the blunt cannula of the infuser and withdrawn from the infuser, respectively.
Figures 12A, 12B:
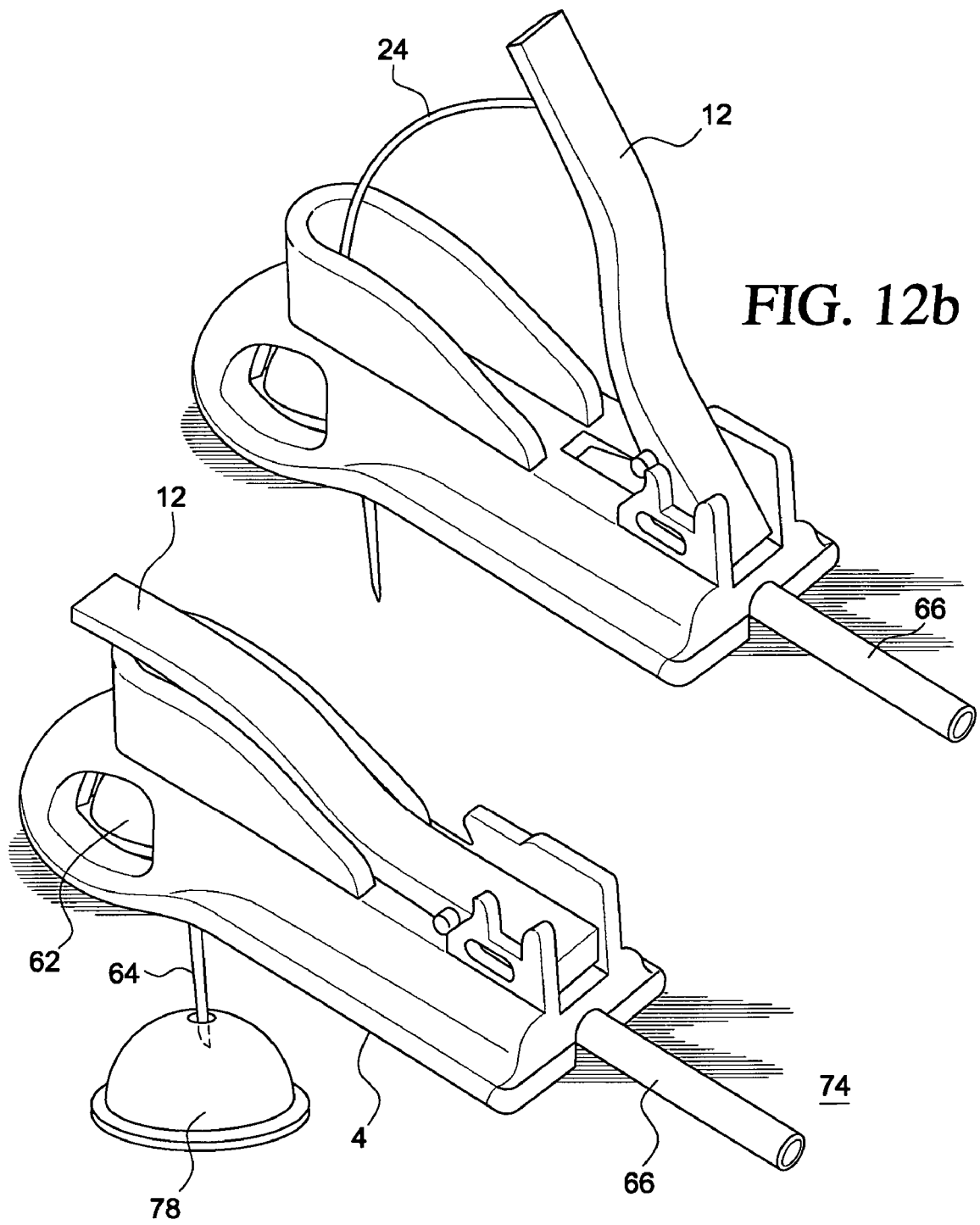
FIG. 12a and FIG. 12b are respective views of the portal access device showing the mating of the sharp cannula to the blunt cannula and the removal of the sharp cannula from the blunt cannula, respectively.

Once it is determined that portal reservoir 78 has been properly punctured and connected to infuser body 62 by way of the concentric blunt/sharp cannulas, the safety needle inserter may be removed from the infuser assembly by lifting arm 12 of the needle inserter relative to its base 4, per shown in FIGS. 11b and 12b. Once tip 24 of needle 24 is positioned within the bore of the base, with the respective lock mechanisms coacting at the arm and the base, arm 12 is prevented from further movement both upwardly and downwardly relative to base 4, as per discussion supra, so that tip 26 of needle 24 is fixedly maintained or positioned within the bore 42 formed in base 4.

Once arm 12 is locked into place, with tip 26 of the needle 24 properly positioned within bore 42 of base 4, the safety needle inserter may be removed from infuser assembly 60. To ensure that infuser body 62 and tube 66 would remain in place while needle inserter 2 is being removed, infuser body 62 may be provided with a pair of wings 82, either by bonding or molding, so that the user can hold wings 82 against the body or the skin surface of the patient, while lifting safety needle inserter 2 away from infuser assembly 60.

After removal of the safety needle inserter 2, infuser assembly 60 may be secured to the skin surface of the patient, by an adhesive layer preformed at the underside of infuser body 62 or an adhesive tape for example, so that a fluid communication path is continuously established between the portal reservoir 78 implanted in the patient and the fluid store 70. As a consequence, medicaments and other fluids are easily and readily infused to the patient through portal reservoir 78 and its associated catheter or tubing 79. Moreover, infuser assembly 60 provides a long term access to the portal reservoir 78 without further risks of sharps injury, as the safety needle inserter 2 has been removed and no further reinsertion is needed. Furthermore, given that the cannula 64 for infuser assembly 60 is a blunt cannula, when the infuser assembly is removed, there is no risk of injury to the patient or the user, and therefore no sharps protection is required.

Yet furthermore, given that septum 68 of the infuser assembly is self-sealing, infuser assembly 60 may be re-accessed through the self-sealing septum 68, either to provide direct coaxial access to the chamber of the portal reservoir 78, or access to the portal outlet catheter 79, for example by a radially flexible and axially stiff (pushable) wire or rod so that the fluid communication path may be threaded or rodded to clear any obstructions that may have occurred in either the portal reservoir or catheter 79 connected to the portal reservoir though which the medicament is fed to the patient.

Moreover, if a particular type of medicament is required, instead of providing the medicament through the fluid store 70, which feeds to tube 66 of the infuser assembly, a right angle needle insertion device such as that described earlier, or as disclosed in the above-discussed '015 patent, may be used to directly access the internal chamber of the portal reservoir, either via the blunt cannula of the infuser assembly or separate from the infuser assembly, so that the particular fluid may be fed through the catheter or tubing connected to the horizontal portion of the right angle needle directly into the portal reservoir. Also, the removal of fluid from the portal reservoir may be effected in the reverse manner by suctioning the fluid in the portal reservoir through a right angle needle inserter, by applying suction to the catheter connected to the horizontal portion of the right angle needle while the vertical portion of the right angle needle is in fluid communication with the portal reservoir.

The invention claimed is:

1. Apparatus comprising a base having a distal portion and a proximal portion, a cannula attached to a first end of an arm, a second end of said arm hingedly connected to the distal portion of said base so that said arm is pivotable relative to said base at its second end, one opening at an upper surface of said base and an other opening at a lower surface of said base provided at the proximal portion of said base wherethrough said cannula passes, a bore defined between said one opening at the upper surface of said base and said other opening at the lower surface of said base, a first lock mechanism provided at the distal portion of said base and a second lock mechanism provided at the second end of said arm, said first and second lock mechanisms coacting to prevent further movement of said arm relative to said base after the tip of said cannula moves past said other opening at the lower surface of said base and is within said bore.

2. Apparatus of claim 1, wherein said second lock mechanism comprises a leg extending from the second end of said arm and wherein first lock mechanism comprises a shoulder at the distal portion of said base, wherein said leg biases against said shoulder to prevent said arm from further downward movement once said arm has been pivoted to a predetermined position whereby the tip of said cannula is positioned within said bore.

3. Apparatus of claim 1, wherein said second lock mechanism comprises a boss extending from the second end of said arm and wherein said first lock mechanism comprises a groove or recess at the distal portion of said base, wherein said boss is caught in and biases against said groove or recess to prevent said arm from further upward movement once said arm has been pivoted to a predetermined position whereby the tip of said cannula is positioned within said bore.

4. Apparatus of claim 1, wherein said second lock mechanism comprises a leg extending from one side of said arm and a boss extending from another side of said arm, and said first lock mechanism comprises a shoulder at one side of the distal portion of said base and a groove or recess provided at an upright at another side of the distal portion of said base; and wherein when said arm is pivoted upwards relative to said base to a predetermined position whereby the tip of said cannula is positioned within said bore, said leg biases against said shoulder to prevent said arm from downward movement and said boss biases against said groove or recess to prevent said arm from further upward movement so that said arm is locked into said predetermined position relative to said base.

5. Apparatus of claim 1, wherein said second end of said arm is hingedly connected to two uprights at the distal portion of said base;

wherein said first lock mechanism comprises:

two fingers extending sideways from said arm proximate to its second end, each of said fingers having at least two stop surfaces;

wherein said second lock mechanism comprises:

a pair of upright guides each extending from said base to face a corresponding one of said uprights, each guide having a notch to which a corresponding one of the fingers from said arm rests when said arm lies horizontally over said base, each guide having a guide surface along which the corresponding one finger of said arm moves when said arm is pivoted upwards away from said base and a stop surface that coacts against one of the stop surfaces of the corresponding one finger when the pivotal movement of said arm positions the tip of said cannula within said bore to thereby prevent said arm from moving in a downward direction; and a recess formed on each front edge of said uprights, said recess coacts against other of the stop surfaces of the corresponding one finger when the pivotal movement of said arm positions the tip of said cannula within said bore to thereby prevent said arm from further upward movement relative to said base.

6. Apparatus of claim 1, further comprising a dam at the proximal portion forward of said one opening and said bore, said dam providing a stop for the first end of said arm for enabling a user to push said cannula into a patient by pressing on said arm.

7. Apparatus of claim 1, wherein said cannula comprises a vertical portion extending downwardly from the first end of said arm and a horizontal portion mounted along the length of said arm, the tip and a substantial portion of said vertical portion extending beyond said opening of said base prior to use.

8. Apparatus of claim 1, further comprising a tube connected to the horizontal portion of said cannula at the second end of said arm for establishing a fluid path whereby fluid is passable between said tube and the tip of said cannula.

9. Apparatus of claim 1, wherein the lower surface of said base is substantially flat to enable said base to lie substantially planarly along the skin of a patient, and wherein said bore extends from said other opening substantially flush with the flat lower surface to said one opening at the upper surface of said base.

10. Apparatus of claim 1, wherein the proximal portion of said base is dome shaped to enable said base to fittingly cover an infuser.

11. A safety needle device, comprising:

a base having a distal portion and a proximal portion, one opening at an upper surface of said base and an other opening at a lower surface of said base provided at the proximal portion of said base, a bore defined between said one opening at the upper surface of said base and said other opening at the lower surface of said base;

an arm having a first end and a second end, the second end of said arm being hingedly connected to the distal portion of said base so that said arm is pivotally movable relative to said base at its second end; and a cannula having a tip extending downwardly from the first end of said arm and passes through said one and other openings of said base before use;

wherein when the first end of said arm is moved to its upmost position, said cannula is withdrawn from said other opening and the tip of said cannula is positioned within said bore.

12. Device of claim 11, further comprising:

a first lock mechanism provided at the distal portion of said base; and a second lock mechanism provided at the second end of said arm;

wherein said first and second lock mechanisms coact to prevent further movement of said arm relative to said base after the tip of said cannula is positioned within said bore.

13. Device of claim 11, wherein said second lock mechanism comprises a leg extending from the second end of said arm and wherein first lock mechanism comprises a shoulder at the distal portion of said base, wherein said leg biases against said shoulder to prevent said arm from downward movement once said arm has been pivoted to a predetermined position whereby the tip of said cannula is positioned within said bore.

14. Device of claim 11, wherein said second lock mechanism comprises a boss extending from the second end of said arm and wherein said first lock mechanism comprises a groove or recess at the distal portion of said base, wherein said boss is caught in and biases against said groove or recess to prevent said arm from further upward movement once said arm has been pivoted to a predetermined position whereby the tip of said cannula is positioned within said bore.

15. Device of claim 11, wherein said second lock mechanism comprises a leg extending from one side of said arm and a boss extending from another side of said arm, and said first lock mechanism comprises a shoulder at one side of the distal portion of said base and a groove or recess provided at an upright at another side of the distal portion of said base; and wherein when said arm is pivoted upwards relative to said base to a predetermined position whereby the tip of said cannula is positioned within said bore, said leg biases against said shoulder to prevent said arm from further downward movement and said boss biases against said groove or recess to prevent said arm from further upward movement so that said arm is locked into said predetermined position relative to said base.

16. Apparatus of claim 11, wherein said second end of said arm is hingedly connected to two uprights at the distal portion of said base;

wherein said first lock mechanism comprises:

two fingers extending sideways from said arm proximate to its second end, each of said fingers having at least two stop surfaces;

wherein said second lock mechanism comprises:

a pair of upright guides each extending from said base to face a corresponding one of said uprights, each guide having a notch to which a corresponding one of the fingers from said arm rests when said arm lies horizontally over said base, each guide having a guide surface along which the corresponding one finger of said arm moves when said arm is pivoted upwards away from said base and a stop surface that coacts against one of the stop surfaces of the corresponding one finger when the pivotal movement of said arm positions the tip of said cannula within said bore to thereby prevent said arm from moving in a downward direction; and a recess formed on each front edge of said uprights, said recess coacts against other of the stop surfaces of the corresponding one finger when the pivotal movement of said arm positions the tip of said cannula within said bore to thereby prevent said arm from further upward movement relative to said base.

17. Device of claim 11, wherein said cannula comprises a right angle cannula having a horizontal portion mounted to said arm and a vertical portion having the tip that is positionable within said bore.

18. Device of claim 17, further comprising a tube connected to the horizontal portion of said cannula at the second end of said arm for establishing a fluid path whereby fluid is passable between said tube and the tip of said cannula.

19. Device of claim 11, wherein the lower surface of said base is substantially flat to enable said base to lie in substantially planarly along the skin of a patient, and wherein said bore extends from said other opening substantially flush with the flat lower surface to said one opening at the upper surface of said base.

20. Device of claim 11, wherein the proximal portion of said base is dome shaped to enable said base to fittingly cover an infuser.

21. A safety needle device, comprising:
- a base having a distal portion and a proximal portion, one opening at an upper surface of said base and an other opening at a lower surface of said base provided at the proximal portion of said base, a bore defined between said one opening at the upper surface of said base and said other opening at the lower surface of said base;
- an arm having a first end and a second end, the second end of said arm being hingedly connected to the distal portion of said base so that said arm is pivotally movable relative to said base at its second end;
- a right angle cannula mounted to said arm, a vertical portion of said cannula including the tip of said cannula extending downwardly from the first end of said arm and passes through said one and other openings of said base before use, a horizontal portion of said cannula mounted along the length of said arm;
- a first lock mechanism having a first and a second part provided at the distal portion of said base; and
- a second lock mechanism having a first and second part provided at the second end of said arm;
- wherein the respective first parts of said first and second lock mechanisms coact to prevent further movement of said arm relative to said base along one direction after the tip of said cannula is positioned within said bore, and wherein the respective second parts of said first and second lock mechanisms coact to prevent further movement of said arm relative to said base along another direction once the tip of said cannula is positioned within said bore.

22. Device of claim 21, further comprising a tube connected to the horizontal portion of said cannula at the second end of said arm for establishing a fluid path whereby fluid is passable between said tube and the tip of said cannula.

23. Device of claim 21, wherein said the lower surface of said base is substantially flat to enable said base to lie substantially planarly along the skin of a patient, and wherein said bore extends from said other opening substantially flush with the flat lower surface to said one opening at the upper surface of said base.

24. Device of claim 21, wherein said first part and said second part of said first lock mechanism comprise a shoulder and a groove or recess, respectively, and wherein said first part and said second part of said second lock mechanism comprises a leg and a boss, respectively; and
- wherein said shoulder and said leg coact to prevent downward movement and said boss and said groove or recess coact to prevent further upward movement of said arm relative to said base when the tip of said cannula is positioned within said bore in said base.

* * * * *